United States Patent [19]

Turner et al.

[11] 4,233,384
[45] Nov. 11, 1980

[54] IMAGING SYSTEM USING NOVEL CHARGE TRANSPORT LAYER

[75] Inventors: S. Richard Turner; John F. Yanus, both of Webster; Damodar M. Pai, Fairport, all of N.Y.

[73] Assignee: Xerox Corporation, Stamford, Conn.

[21] Appl. No.: 34,817

[22] Filed: Apr. 30, 1979

[51] Int. Cl.$^3$ .............................................. G03G 5/04
[52] U.S. Cl. ........................................ 430/59; 430/72
[58] Field of Search ................................... 430/59, 72

[56] References Cited

U.S. PATENT DOCUMENTS

| | | | |
|---|---|---|---|
| T888,013 | 7/1971 | Gilman | 96/1.5 |
| 3,037,861 | 6/1962 | Hoegl et al. | 96/1 |
| 3,041,166 | 6/1962 | Bardeen | 96/1 |
| 3,121,006 | 2/1964 | Middleton et al. | 96/1 |
| 3,121,007 | 2/1964 | Middleton et al. | 96/1 |
| 3,165,405 | 1/1965 | Hoesterey | 96/1 |
| 3,265,496 | 8/1966 | Fox | 96/1 |
| 3,312,548 | 4/1967 | Straughan | 96/1.5 |
| 3,598,582 | 8/1971 | Herrick | 96/1.5 |
| 4,047,949 | 9/1977 | Horgan | 430/59 |
| 4,081,274 | 3/1978 | Horgan | 430/59 |
| 4,140,529 | 2/1979 | Pai et al. | 430/59 |

FOREIGN PATENT DOCUMENTS

763540 2/1971 Belgium.

OTHER PUBLICATIONS

Berwick et al., Research Disclosure, vol. 133 pp. 38-43 (May 1975).

*Primary Examiner*—Jack P. Brammer
*Attorney, Agent, or Firm*—Harvey M. Brownrout; James Paul O'Sullivan

[57] ABSTRACT

A photosensitive member having at least two electrically operative layers is disclosed. The first layer comprises a photoconductive layer which is capable of photogenerating holes and injecting photogenerated holes into a contiguous charge transport layer. The charge transport layer comprises a polycarbonate resin containing from about 25 to about 75 percent by weight of one or more of a compound having the general formula:

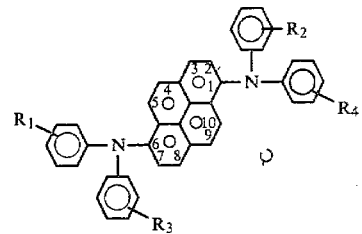

wherein $R_1$, $R_2$, $R_3$ and $R_4$ are selected from the group consisting of hydrogen, an ortho, meta or para alkyl group having from 1 to about 4 carbon atoms, an ortho, meta or para halogen atom, a para phenyl group and combinations thereof.

6 Claims, 4 Drawing Figures

IMAGING SYSTEM USING NOVEL CHARGE TRANSPORT LAYER

BACKGROUND OF THE INVENTION

This invention relates in general to xerography and, more specifically, to a novel photoconductive device and method of use.

In the art of xerography, a xerographic plate containing a photoconductive insulating layer is imaged by first uniformly electrostatically charging its surface. The plate is then exposed to a pattern of activating electromagnetic radiation such as light, which selectively dissipates the charge in the illuminated areas of the photoconductive insulator while leaving behind a latent electrostatic image in the nonilluminated areas. This latent electrostatic image may then be developed to form a visible image by depositing finely divided electroscopic marking particles on the surface of the photoconductive insulating layer.

A photoconductive layer for use in xerography may be a homogeneous layer of a single material such as vitreous selenium or it may be a composite layer containing a photoconductor and another material. One type of composite photoconductive layer used in xerography is illustrated by U.S. Pat. No. 3,121,006 which describes a number of layers comprising finely divided particles of a photoconductive inorganic compound dispersed in an electrically insulating organic resin binder. In its present commercial form, the binder layer contains particles of zinc oxide uniformly dispersed in a resin binder and coated on a paper backing.

In the particular examples described in '006, the binder comprises a material which is incapable of transporting injected charge carriers generated by the photoconductor particles for any significant distance. As a result, with the particular material disclosed, the photoconductor particles must be, in substantially continuous particle-to-particle contact throughout the layer in order to permit the charge dissipation required for cyclic operation. Therefore, with the uniform dispersion of photoconductor particles described, a relatively high volume cencentration of photoconductor, about 50 percent by volume, is usually necessary in order to obtain sufficient photoconductor particle-to-particle contact for rapid discharge. However, it has been found that high photoconductor loadings in the binder results in the physical continuity of the resin being destroyed, thereby significantly reducing the mechanical properties of the binder layer. Systems with high photoconductor loadings are often characterized as having little or no flexibility. On the other hand, when the photoconductor concentration is reduced appreciably below about 50 percent by volume, the photoinduced discharge rate is reduced, making high speed cyclic or repeated imaging difficult or impossible.

U.S. Pat. No. 3,037,861 to Hoegl et al teaches that poly(N-vinylcarbazole) exhibits some long-wave length U.V. sensitivity and suggests that its spectral sensitivity can be extended into the visible spectrum by the addition of dye sensitizers. The Hoegl et al patent further suggests that other additives such as zinc oxide and titanium dioxide may also be used in conjunction with poly(N-vinylcarbazole). In the Hoegl et al patent, the poly(N-vinylcarbazole) is intended to be used as a photoconductor, with or without additive materials which extend its spectral sensitivity.

In addition to the above, certain specialized layered structures particularly designed for reflex imaging have been proposed. For example, U.S. Pat. No. 3,165,405 to Hoesterey utilizes a two-layered zinc oxide binder structure for reflex imaging. The Hoesterey patent utilizes two separate contiguous photoconductive layers having different spectral sensitivites in order to carry out a particular reflex imaging sequence. The Hoesterey device utilizes the properties of multiple photoconductive layers in order to obtain the combined advantages of the separate photoresponse of the respective photoconductive layers.

It can be seen from a review of the conventional composite photoconductive layers cited above, that upon exposure to light, photoconductivity in the layered structure is accomplished by charge transport through the bulk of the photoconductive layer, as in the case of vitreous selenium (and other homogeneous layered modifications). In devices employing photoconductive binder structures which include inactive electrically insulating resins such as those described in the U.S. Pat. No. 3,121,006, conductivity or charge transport is accomplished through high loadings of the photoconductive pigment and allowing particle-to-particle contact of the photoconductive particles. In the case of photoconductive particles dispersed in a photoconductive matrix, such as illustrated by U.S. Pat. No. 3,121,007, photoconductivity occurs through the generation and transport of charge carriers in both the photoconductive matrix and the photoconductor pigment particles.

Although the above patents rely upon distinct mechanisms of discharge throughout the photoconductive layer, they generally suffer from common deficiencies in that the photoconductive surface during operation is exposed to the surrounding environment, and particularly in the case of repetitive xerographic cycling where these photoconductive layers are susceptible to abrasion, chemical attack, heat and multiple exposure to light. These effects are characterized by a gradual deterioration in the electrical characteristics of the photoconductive layer resulting in the printing out of surface defects and scratches, localized areas of persistent conductivity which fail to retain an electrostatic charge, and high dark discharge.

In addition to the problems noted above, these photoreceptors require that the photoconductor comprise eith a hundred percent of the layer, as in the case of the vitreous selenium layer, or that they preferably contain a high proportion of photoconductive material in the binder configuration. The requirements of a photoconductive layer containing all or a major proportion of a photoconductive material further restricts the physical characteristics of the final plate, drum or belt in that the physical characteristics such as flexibility and adhesion of the photoconductor to a supporting substrate are primarily dictated by the physical properties of the photoconductor, and not by the resin or matrix material which is preferably present in a minor amount.

Another form of a composite photosensitive layer which has also been considered by the prior art includes a layer of photoconductive material which is covered with a relatively thick plastic layer and coated on a supporting substrate.

U.S. Pat. No. 3,041,166 to Bardeen describes such a configuration in which a transparent plastic material overlies a layer of vitreous selenium which is contained on a supporting substrate. In operation, the free surface of the transparent plastic is electrostatically charged to a given polarity. The device is then exposed to activating radiation which generates a hole electron pair in the photoconductive layer. The electrons move through the plastic layer and neutralize positive charges on the free surface of the plastic layer thereby creating an electrostatic image. Bardeen, however, does not teach any specific plastic materials which will function in this manner, and confines his examples to structures which use a photoconductor material for the top layer.

U.S. Pat. No. 3,598,582 to Herrick et al describes a special purpose composite photosensitive device adapted for reflex exposure by polarized light. One embodiment which employs a layer of dichroic organic photoconductive particles arrayed in oriented fashion on a supporting substrate and a layer of poly(N-vinylcarbazole) formed over the oriented layer of dichroic material. When charged and exposed to light polarized perpendicular to the orientation of the dichroic layer, the oriented dichroic layer and poly(N-vinylcarbazole) layer are both substantially transparent to the initial exposure light. When the polarized light hits the white background of the document being copied, the light is depolarized, reflected back through the device and absorbed by the dichroic photoconductive material. In another embodiment, the dichroic photoconductor is dispersed in oriented fashion throughout the layer of poly(N-vinylcarbazole).

Belgium Pat. No. 763,540, issued Aug. 26, 1971, discloses an electrophotographic member having at least two electrically operative layers. The first layer comprises a photoconductive layer which is capable of photogenerating charge carriers and injecting the photogenerated holes into a contiguous active layer. The active layer comprises a transparent organic material which is substantially nonabsorbing in the spectral region of intended use, but which is "active in that it allows injection of photogenerated holes from the photoconductive layer, and allows these holes to be transported through the active layer. The active polymers may be mixed with inactive polymers or nonpolymeric material.

Gilman, Defensive Publication of Ser. No. 93,449, filed Nov. 27, 1970, published in 888 O.G. 707 on July 20, 1970, Defensive Publication No. P888.013, U.S. Cl. 96/1.5, discloses that the speed of an inorganic photoconductor such as amorphous selenium can be improved by including an organic photoconductor in the electrophotographic element. For example, an insulating resin binder may have $TiO_2$ dispersed therein or it may be a layer of amorphous selenium. This layer is overcoated with a layer of electrically insulating binder resin having an organic photoconductor such as 4,4'-diethylamino-2,2'-dimethyltriphenylmethane dispersed therein.

"Multi-Active Photoconductive Element", Martin A. Berwick, Charles J. Fox and William A. Light, Research Disclosure, Vol. 133; pages 38–43, May 1975, was published by Industrial Opportunities Ltd., Homewell, Havant, Hampshire, England. This disclosure relates to a photoconductive element having at least two layers comprising an organic photoconductor containing a charge transport layer in electrical contact with an aggregate charge generation layer. Both the charge generation layer and the charge transport layer are essentially organic compositions. The charge generation layer contains a continuous, electrically insulating polymer phase and a discontinuous phase comprising a finely divided, particulate cocrystalline complex of (1) at least one polymer having an alkylidene diarylene group in a recurring unit and (2) at least one pyrylium-type dye salt. The charge transport layer is an organic material which is capable of accepting and transporting injected charge carriers from the charge generation layer. This layer may comprise an insulating resinous material having 4,4'-bis(diethylamino)-2,2'-dimethyltriphenylmethane dispersed therein.

U.S. Pat. No. 3,265,496, discloses that N,N,N',N'-tetraphenylbenzidine may be used as photoconductive material in electrophotographic elements. This compound is not sufficiently soluble in the resin binders of the instant invention to permit a sufficient rate of photo-induced discharge.

Straughan, U.S. Pat. No. 3,312,548, in pertinent part, discloses a xerographic plate having a photoconductive insulating layer comprising a composition of selenium, arsenic and a halogen. The halogen may be present in amounts from about 10 to 10,000 parts per million. This patent further discloses a xerographic plate having a support, a layer of selenium and an overlayer of a photoconductive material comprising a mixture of vitreous selenium, arsenic and a halogen.

In the context of a dual layer system, i.e. a charge generating layer and a charge transporting layer, most organic charge transporting layers using active materials dispersed in organic binder materials have been found to trap charge carriers causing an unacceptable buildup of residual potential when used in a cyclic mode in electrophotography. Also, most organic charge transporting materials known when used in a layered configuration contiguous to a charge generating layer have been found to trap charge at the interface between the two layers. This results in lowering the potential differences between the illuminated and nonilluminated regions when these structures are exposed to an image. This, in turn, lowers the print density of the end product, i.e. the electrophotographic copy.

Another consideration which is necessary in the system is the glass transition temperature ($T_g$). The ($T_g$) of the transport layer has to be substantially higher than the normal operating temperatures. Many organic charge transporting layers using active materials dispersed in organic binder material have unacceptably low ($T_g$) at loadings of the active material in the organic binder material which is required for efficient charge transport. This results in the softening of the layer, which in turn, may become susceptible to impaction of dry developers and toners. Another unacceptable feature of a low ($T_g$) is the case of leaching or exudation of the active materials from the organic binder material resulting in degradation of charge transport properties from the charge transport layer. Another deficiency of the low ($T_g$) layers is the susceptibility to crystallization resulting from increased diffusion rates of the small molecules.

Another consideration for the use of organic transport layers in electrophotography is the value of the charge carriers mobilities. Most of the organics known to date are deficient in this respect in that they set a limit to the cyclic speed of the system employing the same. None of the references above overcome the foregoing problems.

OBJECTS OF THE INVENTION

It is an object of this invention to provide a novel photoconductive device adapted for cyclic imaging which overcomes the above-noted disadvantages.

It is another object of this invention to provide a novel imaging member capable of remaining flexible while still retaining its electrical properties after extensive cycling and exposure to the ambient, i.e., oxygen, ultraviolet radiation, elevated temperatures, etc.

It is another object of this invention to provide a novel imaging member which has no bulk trapping of charge upon extensive cycling.

SUMMARY OF THE INVENTION

The foregoing objects and others are accomplished in accordance with this invention by providing a photoconductive member having at least two operative layers. The first layer comprises a layer of photoconductive material which is capable of photogenerating and injecting photogenerated holes into a contiguous or adjacent electrically active layer. The electrically active material comprises a polycarbonate resin material having dispersed therein from about 25 to about 75 percent by weight of one or more compounds having the general formula:

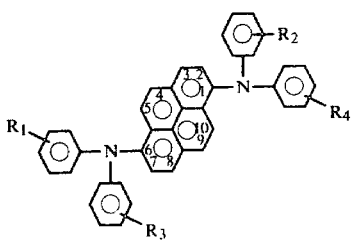

wherein $R_1$, $R_2$, $R_3$ and $R_4$ are selected from the group consisting of hydrogen, an ortho, meta or para alkyl group having from 1 to about 4 carbon atoms (e.g. methyl, ethyl, propyl, isopropyl, isobutyl, tert-butyl, n-butyl), an ortho, meta or para halogen atom (e.g. chlorine, fluorine or bromine), a para phenyl group and combinations thereof. At least two of the four N substituents must in turn be substituted with said alkyl group, said halogen atom or said para phenyl group or a combination of these substituents. Thus, either $R_1$ and $R_2$ or $R_3$ and $R_4$ or $R_1$, $R_2$, $R_3$ and $R_4$ will be so substituted.

The structure shown above is the pyrenyl-1,6-diamine isomer. It is possible that there is some small percentage of the 1,8 isomer.

Included within this structure are the following compounds: N,N'-diphenyl-N,N'-bis(3-methylphenyl)-pyrenyl-1,6-diamine; N,N'-diphenyl-N,N'-bis(3-ethylphenyl)-pyrenyl-1,6-diamine; N,N'-diphenyl-N,N'-bis(3-tert-butylphenyl)-pyrenyl-1,6-diamine; N,N'-diphenyl-N,N'-bis(3-chlorophenyl)-pyrenyl-1,1-diamine. Different alkyl groups may be substituted in the same molecule and chloro and alkyl group may be substituted in the same molecule. The above described small molecules, due to the presence of solubilizing groups, such as methyl or chlorine are substantially more soluble in the polycarbonate resin binders described herein than unsubstituted species.

The active overcoating layer, i.e. the charge transport layer, is substantially nonabsorbing to visible light or radiation in the region of intended use but is "active" in that it allows the injection of photogenerated holes from the photoconductive layer, i.e., charge generation layer, and allows these holes to be transported through the active charge transport layer to selectively discharge a surface charge on the surface of the active layer.

It was found that, unlike the prior art, when the diamines of the instant invention were dispersed in a polycarbonate binder, this layer transports charge very efficiently without any trapping of charges when subjected to charge/light discharge cycles in an electrophotographic mode. There is no buildup of the residual potential over many thousands of cycles.

Furthermore, the transport layers comprising the diamines of the instant invention dispersed in a polycarbonate binder were found to have sufficiently high ($T_g$) even at high loadings thereby eliminating the problems associated with low ($T_g$). The prior art suffers from this deficiency.

Furthermore, no deterioration in charge transport was observed when these transport layers were subjected to ultraviolet radiation encountered in its normal usage in a xerographic machine environment.

Therefore, when members containing charge transport layers of the instant invention are exposed to ambient conditions, i.e., oxygen, U.V. radiation, etc., these layers remain stable and do not lose their electrical properties. Furthermore, the diamines of the instant invention do not crystallize and become insoluble in the polycarbonate resinous material into which these materials were originally dispersed. Therefore, since the diamines of the instant invention do not appreciably react with oxygen or are not affected by U.V. radiation, encountered in their normal usage in a xerographic machine environment, then when combined with a polycarbonate resin, it allows acceptable injection of photogenerated holes from the photoconductor layer, i.e., charge generation layer, and allows these holes to be transported repeatedly through the active layer sufficiently to acceptably discharge a surface charge on the free surface of the active layer in order to form an acceptable electrostatic latent image.

As mentioned, the foregoing objects and others may be accomplished in accordance with this invention by providing a specifically preferred photoconductive member having at least two operative layers. The first layer being a preferred specie which consists essentially of a mixture of amorphous selenium, arsenic and a halogen. Arsenic is present in amounts from about 0.5 percent to about 50 percent by weight and the halogen is present in amounts from about 10 to about 10,000 parts per million with the balance being amorphous selenium. This layer is capable of photogenerating and injecting photogenerated holes into a contiguous or adjacent charge transport layer. The charge transport layer consists essentially of a polycarbonate resinous material having dispersed therein from about 25 to about 75 percent by weight of the diamines of the instant invention.

"Electrically active" when used to define the active layer means that the material is capable of supporting the injection of photogenerated holes from the generating material and capable of allowing the transport of these holes through the active layer in order to discharge a surface charge on the active layer.

"Electrically inactive" when used to describe the organic material which does not contain any diamine of the instant invention means that the material is not capable of supporting the injection of photogenerated holes from the generating material and is not capable of allowing the transport of these holes through the material.

It should be understood that the polycarbonate resinous material which becomes electrically active when it contains from about 25 to about 75 percent by weight of the diamine does not function as a photoconductor in the wavelength region of intended use. As stated above, hole electron pairs are photogenerated in the photoconductive layer and the holes are then injected into the active layer and hole transport occurs through this active layer.

A typical application of the instant invention involves the use of a layered configuration member which in one embodiment comprises a supporting substrate, such as a conductor, containing a photoconductive layer thereon. For example, the photoconductive layer may be in the form of amorphous, or trigonal selenium or alloys of selenium such as selenium-arsenic, selenium-tellurium-arsenic and selenium-tellurium. A charge transport layer of electrically inactive polycarbonate resinous material, having dispersed therein from about 25 percent to about 75 percent by weight of the diamine is coated over the selenium photoconductive layer. Generally, a thin interfacial barrier or blocking layer is sandwiched between the photoconductive layer and the substrate. The barrier layer may comprise any suitable electrically insulating material such as metallic oxide or organic resin. The use of the polycarbonate containing the diamine allows one to take advantage of placing a photoconductive layer adjacent to a supporting substrate and physically protecting the photoconductive layer with a top surface which will allow for the transport of photogenerated holes from the photoconductor. This structure can then be imaged in the conventional xerographic manner which usually includes charging, exposure and development.

As mentioned, when an alloy of selenium and arsenic containing a halogen of the instant invention is used as a charge carrier generation layer in a multilayered device which contains a contiguous charge carrier transport layer, the member, as a result of using this particular charge generation layer has unexpectedly high contrast potentials as compared to similar multilayered members using different generator layer materials.

In general, the advantages of the improved structure and method of imaging will become apparent upon consideration of the following disclosure of the invention, especially when taken in conjunction with the accompanying drawings wherein:

DETAILED DESCRIPTION OF THE DRAWINGS

Figure 1:
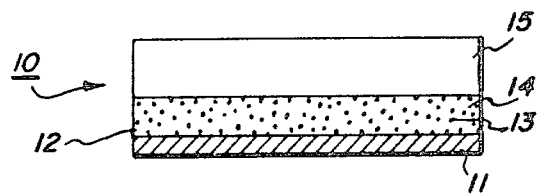
FIG. 1 is a schematic illustration of one embodiment of a device of the instant invntion.

In the drawings, FIGS. 1-4 represent several variations of photoreceptor plates within the scope of the invention. They are all basically similar in that they comprise a substrate, a charge generation layer thereon and a charge transport layer over the generation layer.

In FIG. 1, photoreceptor 10 consists of a substrate 11; a charge generator layer 12 comprising photoconductive particles 13 dispersed randomly in an electrically insulating organic resin 14; and a charge transport layer 15 comprising a transparent electrically inactive polycarbonate resin having dissolved therein one or more of the diamines defined above.

Figure 2:
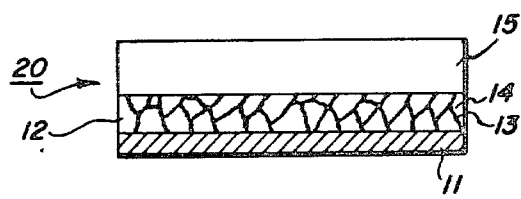
FIG. 2 illustrates a second embodiment of the device for the instant invention.

In FIG. 2, photoreceptor 20 differs from FIG. 1 in the charge generator layer 12. Here the photoconductive particles are in the form of continuous chains through the thickness of the binder material 14. The chains constitute a multiplicity of interlocking photoconductive continuous paths through the binder material. The photoconductive paths are present in a volume concentration of from about 1 to 25 percent based on the volume of said layer.

Figure 3:
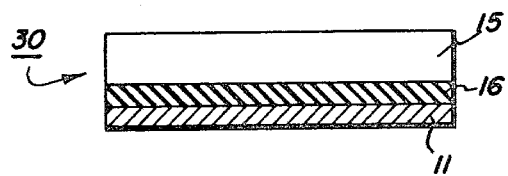
FIG. 3 illustrates a third embodiment of the device of the instant invention.

In FIG. 3, photoreceptor 30 differs from FIGS. 1 and 2 in that charge generator layer 16 comprises a homogeneous photoconductive layer 16.

Figure 4:
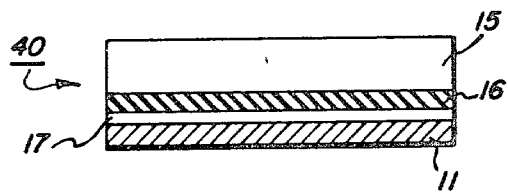
FIG. 4 illustrates a fourth embodiment of the device of the instant invention.

In FIG. 4, photoreceptor 40 differs from FIG. 3 in that a blocking layer 17 is employed at the substrate-photoreceptor interface. The blocking layer functions to prevent the injection of charge carriers from the substrate into the photoconductive layer. Any suitable material may be used, e.g. Nylon, epoxy and aluminum oxide.

In the devices of the present invention the substrate II may be of any suitable conductive material, e.g. aluminum, steel, brass, graphite, dispersed conductive salts, conductive polymers or the like. The substrate may be rigid or flexible, and of any conventional thickness. Typical substrate forms include flexible belts or sleeves, sheets, webs, plates, cylinders and drums. The substrate may also comprise a composite structure such as a thin conductive layer, such as aluminum or copper iodide, or glass coated with a thin conductive coating of chromium or tin oxide. Particularly preferred as substrates are metallized polyesters, such as aluminized Mylar.

In addition, an electrically insulating substrate may be used. In this instance, the charge may be placed upon the insulating member by double corona charging techniques, well known and disclosed in the art. Other modifications using an insulating substrate or no substrate at all include placing the imaging member on a conductive backing member or plate and charging the surface while in contact with said backing member. Subsequent to imaging, the imaging member may then be stripped from the conductive backing. The photoconductive material which may be the particles 13 of FIGS. 1 and 2 or the homogeneous layer 16 of FIGS. 3 and 4 may consist of any suitable inorganic or organic photoconductor and mixtures thereof. Inorganic materials include inorganic crystalline photoconductive compounds and inorganic photoconductive glasses. Typical inorganic compounds include cadmium sulfoselenide, cadmium selenide, cadmium sulfide and mixtures thereof. Typical inorganic photoconductive glasses include amorphous selenium and selenium alloys such as selenium-tellurium, selenium-tellurium-arsenic and selenium-arsenic and mixtures thereof. Selenium may also be used in a crystalline form known as trigonal selenium.

Typical organic photoconductive materials which may be used as charge generators include phthalocyanine pigment such as the X-form of metal-free phthalocyanine described in U.S. Pat. No. 3,357,989 to Bryne et al; metal phthalocyanines such as copper phthalocyanine; quinacridones available from DuPont under the tradename Monastral Red, Monastral Violet and Monastral Red Y; substituted 2,4-diamino-triazines disclosed by Weinberger in U.S. Pat. No. 3,445,227; triphenodioxazines disclosed by Weinberger in U.S. Pat. No. 3,442,781; polynuclear aromatic quinones available from Allied Chemical Corporation under the tradename Indofast Double Scarlet, Indofast Violet Lake B, Indofast Brilliant Scarlet and Indofast Orange.

Additionally, intramolecular charge transfer complexes may be poly(N-vinylcarbazole) (PVK) and trinitrofluorenone (TNF) may be used as charge generating materials. These materials are capable of injecting photogenerated holes into the transport material.

Additionally, intramolecular charge transfer complexes may be used as charge generation materials capable of injecting photogenerated holes into the transport materials.

A preferred generator material is trigonal selenium. A method of making a photosensitive imaging device utilizing trigonal selenium comprises vacuum evaporating a thin layer of vitreous selenium onto a substrate, forming a relatively thicker layer of electrically active organic material over said selenium layer, followed by heating the device to an elevated temperature, e.g., 125° C. to 210° C., for a sufficient time, e.g., 1 to 24 hours, sufficient to convert the vitreous selenium to the crystalline trigonal form. Another method of making a photosensitive member which utilizes trigonal selenium comprises forming a dispersion of finely divided vitreous selenium particles in a liquid organic resin solution and then coating the solution onto a supporting substrate and drying to form a binder layer comprising vitreous selenium particles contained in an organic resin matrix. Then the member is heated to an elevated temperature, e.g., 100° C. to 140° C. for a sufficient time, e.g., 8 to 24 hours, which converts the vitreous selenium to the crystalline trigonal form. Similarly, finely divided trigonal selenium particles dispsersed in an organic resin solution can be coated onto a supporting substrate and dried to form a generator binder layer.

Another preferred embodiment is a 0.2 micron thick charge generation layer of 35.5 percent by weight arsenic, 64.5 percent by weight amorphous selenium and 850 parts per million iodine. This charge generation layer may be overcoated with a 30 micron thick charge transport layer of Makrolon ®, a polycarbonate resin, which has dispersed therein 40 percent by weight of the diamine of the instant invention.

The above list of photoconductors should in no way be taken as limiting, but merely illustrative as suitable materials. The size of the photoconductive particles is not particularly critical; but particles in a size range of about 0.01 to 5.0 microns yield particularly satisfactory results.

Binder material 14 may comprise any electrically insulating resin such as those described in the above-mentioned Middleton et al U.S. Pat. No. 3,121,006. When using an electrically inactive or insulating mesh, it is essential that there be particle-to-particle contact between the photoconductive particles. This necessitates that the photoconductive material be present in an amount of at least about 10 percent by volume of the binder layer with no limitation on the maximum amount of photoconductor in the binder layer. If the matrix or binder comprises an active material, the photoconductive material need only to comprise about 1 percent or less by volume of the binder layer with no limitation on the maximum amount of the photoconductor in the binder layer. The thickness of the photoconductive layer is not critical. Layer thicknesses from about 0.05 to 20.0 microns have been found satisfactory, with a preferred thickness of about 0.1 to 5.0 microns yielding good results.

Another embodiment is where the photoconductive material may be particles of amorphous selenium-arsenic-halogen as shown as particles 13 which may comprise from about 0.5 percent to about 50 percent by weight arsenic and the halogen may be present in amounts from about 10 to 10,000 parts per million with the balance being selenium. The arsenic preferably may be present from about 20 percent to about 40 percent by weight with 35.5 percent by weight being the most preferred. The halogen preferably may be iodine, chlorine or bromine. The most preferred halogen is iodine. The remainder of the alloy or mixture is preferably selenium.

Active layer 15 comprises a transparent electrically inactive polycarbonate resinous material having dispersed therein from about 25 to 75 percent by weight of one or more of the diamines defined above.

In general, the thickness of active layer 15 should be from about 5 to 100 microns, but thicknesses outside this range can also be used.

The preferred polycarbonate resins for the transport layer have a molecular weight from about 20,000 to about 120,000, more preferably from about 50,000 to about 120,000.

The materials most preferred as the electrically inactive resinous material are poly(4,4'-isopropylidene-diphenylene carbonate) having molecular weights of from about 25,000 to about 40,000, available as Lexan ® 145, and from about 40,000 to about 45,000, available as Lexan ® 141, both from the General Electric Company; and from 50,000 to about 120,000, available as Makrolon ®, from Farbenfabricken Bayer A.G.; and from about 20,000 to about 50,000, available as Merlon ®, from Mobay Chemical Company.

Active layer 15, as described above, is essentially nonabsorbing to light in the wavelength region employed to generate carriers in the photoconductive layer. This preferred range for xerographic utility is from about 4,000 to about 8,000 angstrom units. In addition, the photoconductor should be responsive to all wavelengths from 4,000 to 8,000 angstrom units if panchromatic responses are required. All photoconductor-active material combinations of the instant invention result in the injection and subsequent transport of holes across the physical interface between the photoconductor and the active material.

The reason for the requirement that active layer 15, i.e., charge transport layer, should be transparent is that most of the incident radiation is utilized by the charge carrier generator layer for efficient photogeneration. This material is further characterized by the ability to transport the carrier even at the lowest electrical fields developed in electrophotography.

The active transport layer which is employed in conjunction with the photoconductive layer in the instant invention is a material which is an insulator to the extent that the electrostatic charge placed on said active transport layer is not conducted in the absence of illumination, i.e., with a rate sufficient to prevent the formation and retention of an electrostatic latent image thereon.

In general, the thickness of the active layer preferably is from about 5 to 100 microns, but thicknesses outside this range can also be used. The ratio of the thickness of the active layer, i.e., charge transport layer, to the photoconductive layer, i.e., charge generator layer, preferably should be maintained from about 2:1 to 200:1 and in some instances as great as 400:1.

The following examples further specifically define the present invention with respect to a method of making a photosensitive member. The percentages are by weight unless otherwise indicated. The examples below are intended to illustrate various preferred embodiments of the instant invention.

EXAMPLE I

Preparation of N,N'diphenyl-N,N'-bis(3-methylphenyl)-pyrenyl-1,6-diamine.

A 250 milliliter three necked round bottom flask equipped with a mechanical stirrer and purged with argon was charged with 11 grams (0.06 moles) 3-methyldiphenylamine, 9.1 grams (0.02 moles) of 1,6-diiodopyrene, 15 grams (0.11 moles) of potassium carbonate, 10 grams of copper bronze and 50 milliliters of $C_{13}$–$C_{15}$ aliphatic hydrocarbons, i.e. Soltrol® 170, from the Phillips Chemical Company. The mixture was heated to 210° C. for 18 hours. The product was isolated by the addition of 200 milliliters of n-octane and hot filtered to remove inorganic solids. The dark green filtrate was column chromatographed using Woelm neutral alumina with benzene as the eluent. The deep yellow solid was extracted with acetone to yield yellow crystals of N,N'-diphenyl-N,N'-bis(3-methylphenyl)-pyrenyl-1,6-diamine having a melting point of 236°–238° C.

Analytical Calculation for $C_{42}H_{32}N_2$:C, 88.36; H, 5.67; N, 4.96.

Found C, 89.09, H, 6.05, N, 4.84.

EXAMPLE II

A photosensitive structure similar to that illustrated in FIG. 4 was prepared as follows:

An aluminized Mylar® substrate was coated with a thin (about 300 Å) barrier adhesive layer of DuPont polyester 4900®. A 0.5 micron layer of amorphous selenium was deposited on the adhesive layer by employing a vacuum of approximately $10^{-5}$ Torr while keeping the aluminum at a temperature of 55° C. Onto the surface of the selenium was coated a 20 micron thick transport layer of the compound of Example I dissolved in Makrolon® polycarbonate. The weight ratio of the compound of Example I to the polycarbonate was 2:3 respectively and it was coated from a solution in methylene chloride. The device was heated in vacuum at 45° C. for 12 hours to remove excess solvent.

The photoreceptor was tested for its xerographic photoconductive characteristics as follows:

The plate was negatively charged to 1250 volts and exposed to a filtered xenon light flash of 5 microseconds duration having a wavelength of 4500 Å and a light intensity of 30 ergs/cm². The device discharged to less than 100 volts in 0.1 seconds. The device was then subjected to standard xerographic charge-expose-erase sequences for about 1000 cycles and no degradation in the charging or discharge was observed.

These properties suggest that the device has adequate characteristics for it to be employed in a fast electrophotographic duplicating machine. This layered photoreceptor structure was employed in a Xerox Model D® Machine and satisfactory developed images are produced.

EXAMPLE III

A layered device as in Example II was prepared with a 0.1 micron thick generator layer of amorphous arsenic triselenide instead of amorphous selenium. The generator layer was prepared by vapor deposition of arsenic triselenide onto a DuPont 49000® polyester adhesive coated aluminum substrate being maintained at 50° C. The remainder of the device is prepared as in Example II.

Satisfactory xerographic photoconductive discharge is observed when the device is negatively corona charged to 1200 volts and exposed to an unfiltered xenon flash source of 5 microseconds duration and a light intensity of 30 ergs/cm². The potential dropped to less than 100 volts in 0.15 seconds as a result of the exposure. Stable operation is observed when the device is subjected to a charge-expose-erase sequence for 1000 cycles.

EXAMPLE IV

A layered device as in Example II was prepared with a 2 micron thick layer of particulate trigonal selenium. This generator layer of particulate trigonal selenium is solvent coated from a slurry of 10 volume percent trigonal selenium dispersed in poly-N-vinylcarbazole. The slurry contained 0.4 gram of selenium, 0.8 gram of poly-N-vinylcarbazole and 14 milliliters of a 1:1 mixture of toluene and tetrahydrofuran. The generator layer is heated in vacuum at 150° C. for 12 hours before the transport layer is applied as in Example II.

The device was tested as in Example III and it exhibited the same excellent characteristics. Compounds within the scope of the generic formula which represents the active material of the transport layer can be prepared by the process of Example I from 1,6-diiodopyrene by utilizing appropriate amine precursors, such as 4-n-butyl diphenylamine, 4,4'-dimethyl diphenylamine, 3,3'-dichlorodiphenylamine and 3,3'-dimethyl diphenylamine.

The invention has been described with particular reference to preferred embodiments thereof but it will be understood that variations and modifications can be effected within the spirit and scope of the invention as described herein-above and as defined in the appended claims.

What is claimed is:

1. An imaging member comprising a charge generation layer comprising a layer of photoconductive material and in contact therewith a charge transport layer of a polycarbonate resin material having dispersed therein from about 25 to about 75 percent by weight of one or more compounds having the general formula:

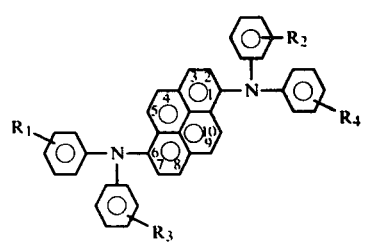

wherein $R_1$, $R_2$, $R_3$ and $R_4$ are selected from the group consisting of hydrogen, an ortho, meta or para alkyl group having from 1 to about 4 carbon atoms, an ortho, meta or para halogen atom, a para phenyl group and combinations thereof, at least two of the four N substituents must in turn be substituted with said alkyl group, said halogen atom or said para phenyl group or a combination of these substituents, said photoconductive layer exhibiting the capability of photogeneration of holes and injection of said holes and said charge transport layer being substantially nonabsorbng in the spectral region at which the photoconductive layer generates and injects photogenerated holes, but being capable of supporting the injection of photogenerated holes from said photoconductive layer and transporting said holes through said charge transport layer.

2. The member of claim 1 wherein the polycarbonate resin has a molecular weight of from about 20,000 to about 120,000.

3. The member of claim 2 wherein the polycarbonate is poly(4,4′-isopropylidene-diphenylene carbonate).

4. The member according to claim 3 wherein the polycarbonate has a molecular weight between from about 25,000 to about 45,000.

5. The member according to claim 3 wherein the polycarbonate has a molecular weight of from about 50,000 to about 120,000.

6. The member of claim 1 wherein said charge transport contains N,N′diphenyl-N,N′bis(3-methylphenyl)-pyrenyl-1,6-diamine.

* * * * *